United States Patent [19]

Parker et al.

[11] Patent Number: 5,250,728
[45] Date of Patent: Oct. 5, 1993

[54] PREPARATION OF ETHYLENEDIAMINETRIACETIC ACID

[75] Inventors: Brian A. Parker, Nashua; Barry A. Cullen, Lyndeborough; Roger R. Gaudette, Hudson, all of N.H.

[73] Assignee: Hampshire Chemical Corp., Lexington, Mass.

[21] Appl. No.: 806,567

[22] Filed: Dec. 12, 1991

[51] Int. Cl.$^5$ .......................................... C07C 229/00
[52] U.S. Cl. .............................. 562/565; 548/300.1; 544/399
[58] Field of Search ......................................... 562/565

[56] References Cited

U.S. PATENT DOCUMENTS

| | | | |
|---|---|---|---|
| 2,407,645 | 9/1946 | Bersworth | 562/565 |
| 2,811,550 | 10/1957 | Young | 562/565 |
| 3,313,779 | 4/1967 | White | 260/59 |
| 3,515,742 | 6/1970 | Morgan et al. | 260/465.5 |
| 3,733,355 | 5/1973 | Harris et al. | 260/534 E |
| 3,758,534 | 9/1973 | Popper et al. | 260/429 |
| 3,988,367 | 10/1976 | Gaudette | 562/565 |
| 4,115,634 | 9/1978 | Bechara et al. | 521/126 |
| 4,622,420 | 11/1986 | Meares | 562/565 |
| 4,704,465 | 11/1987 | Lannert et al. | 558/346 |

FOREIGN PATENT DOCUMENTS 59-22879 5/1979 Japan .

OTHER PUBLICATIONS

Chem. Abstracts vol. 62, 9129(d), 1965.
Chem. Abstracts vol. 71, 18369c, 1969.
Chem. Abstracts vol. 92, 215062g, 1980.
Chem. Abstracts vol. 67, 22433d, 1967.

Primary Examiner—Michael L. Shippen
Attorney, Agent, or Firm—Nields & Lemack

[57] ABSTRACT

Synthesis of ethylenediaminetriacetic acid (ED3A) or its salts is disclosed. A salt of N,N'-ethylenediaminediacetic acid (ED2AH$_2$) is condensed with formaldehyde to form a stable 5-membered ring intermediate. The addition of cyanide across this cyclic material forms ethylenediamine N,N'-diacetic acid-N'-cyanomethyl or salts thereof (mononitrile-diacid). The nitrile in aqueous solutions may be spontaneously cyclized to form 2-oxo-1,4-piperazinediacetic acid (3KP) or salts thereof, which is the desired cyclic intermediate. In the presence of excess base, salts of ED3A are formed in excellent yield and purity. Alternatively, the starting material is ED2AH$_a$X$_b$, where x is a base cation, e.g., an alkali or alkaline earth metal, a is 1 to 2, and b is 0 to 1 in aqueous solutions. The reaction mixture also can be acidified to ensure complete formation of carboxymethyl-2-oxopiperazine (the lactam) prior to the reaction. Formaldehyde is added, essentially resulting in the hydroxymethyl derivative. On the addition of a cyanide source, 1-cyanomethyl-4-carboxymethyl-2-ketopiperazine (mononitrile diacid) or a salt thereof is formed. Upon the addition of any suitable base or acid, this material may be hydrolyzed to 3KP. The addition of a base will open this ring structure to form the salt of ED3A.

10 Claims, No Drawings

PREPARATION OF ETHYLENEDIAMINETRIACETIC ACID

BACKGROUND OF THE INVENTION

Ethylenediaminetriacetic acid (ED3A) or its salts (such as ED3ANa₃) has applications in the field of chelating chemistry, and may be used as a starting material in the preparation of strong chelating polymers, oil soluble chelants, surfactants and others. Conventional routes for the synthesis of ethylenediaminetriacetic acid were achieved via its N-benzyl derivative, which was subsequently hydrolyzed in alkaline solutions to ED3ANa₃, thus avoiding cyclization to its 2-oxo-1,4-piperazinediacetic acid (3KP) derivative. Syntheses attempted by both the alkaline condensation of chloroacetic acid with ethylenediamine, and the carboxymethylation of the diamine with formaldehyde and sodium cyanide resulted in complex mixtures requiring complex extraction techniques (e.g. almost exclusive solubility of 3KP in boiling dimethylformamide, Can. J. Chemistry 1970, 48 (1), 163–175) to generate the desired product, and then in only relatively poor yield. In addition, conventional processes resulted in large quantities of byproduct, such as ethylenediaminetetraacetic acid (ED4A). Where the by-products were especially objectionable, complicated blocking techniques were necessary in order to achieve a relatively pure solution.

One example of the synthesis of ethylenediamine-N,N,N'-triacetic acid is shown in Chemical Abstracts 78, Vol. 71, page 451, no. 18369c, 1969. There it is disclosed that ethylenediamine reacts with $ClH_2CCO_2H$ in a 1:3 molar ratio in basic solution at 10° C. for 24 hours to form a mixture from which ethylenediamine-N,N,N'-triacetic acid can be separated by complexing the same with Co(III). The resulting cobalt complexes can be isolated through ion exchange.

It is therefore desirable to produce ethylenediaminetriacetic acid or its salts in high conversions and excellent yield.

SUMMARY OF THE INVENTION

The problems of the prior art have been overcome by the instant invention, which provides a simple process for the synthesis of ED3A or its salts. Specifically, a salt of N,N'-ethylenediaminediacetic acid (ED2AH₂) is condensed with formaldehyde to form a stable 5-membered ring intermediate. The addition of cyanide across this cyclic material forms ethylenediamine N,N'-diacetic acid-N'-cyanomethyl or salts thereof (mononitrile-diacid). The nitrile in aqueous solutions may be spontaneously cyclized to form 3KP or salts thereof, which is the desired cyclic intermediate. In the presence of excess base, salts of ED3A are formed in excellent yield and purity.

In an alternative embodiment, the starting material is $ED2AH_aX_b$, where X is a base cation, e.g., an alkali or alkaline earth metal, a is 1 to 2, and b is 0 to 1 in aqueous solutions. The reaction mixture also can be acidified to ensure complete formation of carboxymethyl-2-oxopiperazine (the lactam) prior to the reaction. Formaldehyde is added, essentially resulting in the hydroxymethyl derivative. On the addition of a cyanide source, 1-cyanomethyl-4-carboxymethyl-2-ketopiperazine (mononitrile monoacid) or a salt thereof is formed. In place of CH₂O and a cyanide source, HOCH₂CN, which is the reaction product of formaldehyde and cyanide, may also be employed in this method. Upon the addition of any suitable base or acid, this material may be hydrolyzed to 3KP. The addition of a base will open this ring structure to form the salt of ED3A.

DETAILED DESCRIPTION OF THE INVENTION

Suitable salts of ethylenediaminediacetic acid useful as the starting material in the first embodiment of the instant invention include alkali and alkaline earth metal salts, in particular, the sodium and potassium salts. For purposes of illustration, the sodium salt will be used, although it should be understood that other salts may be employed without departing from the spirit and scope of the invention. Step I in the overall reaction scheme is the alkaline condensation of formaldehyde with N,N'-ethylenediamine disodium acetate to form a 5-membered ring structure, 1,3-bis(carboxymethyl)imidazolidine, and is illustrated as follows:

Step I

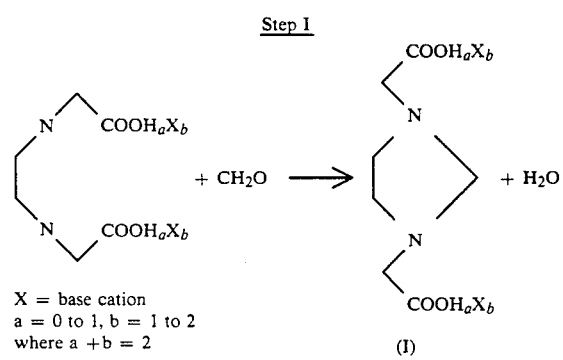

X = base cation
a = 0 to 1, b = 1 to 2
where a + b = 2

(I)

The above reaction may be carried out in the presence of additional base. Suitable bases include alkali and alkaline earth metal hydroxides, preferably sodium and potassium hydroxide. Compound (I) is the bridged reaction product of $EDDANa_{(1.0 \rightarrow 2.0)}$ and formaldehyde, which the present inventor has found to be a stable intermediate in the ED3A synthesis. Compound (I) is formed easily between 0° and 110° C. The Step I reaction proceeds quickly and forms readily at pH's greater than about 7.0. Preferably the temperature employed is about 0° to 65° C., most preferably 15° to 65° C., although temperatures higher than 65° C. are operable. Formaldehyde can be used in stoichiometric amounts, although it is preferred that a slight molar excess be used, preferably 0.5%–2.0%. Preferably the concentration of the formaldehyde is 55% or less in aqueous solution. Paraformaldehyde also can be used.

The second step in the reaction scheme is illustrated below:

Step II

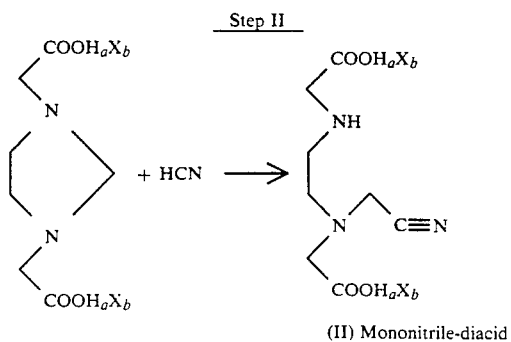

(II) Mononitrile-diacid

Compound (II) is readily formed at temperature between 0° and 110° C. The reaction should be conducted at temperatures at or below the boiling point of the solution. Preferably the reaction is carried out at temperatures from about 0° to about 65° C., most preferably about 15° to 65° C. to enhance the reaction rate. Suitable sources of cyanide include gaseous hydrogen cyanide, an aqueous solution of hydrogen cyanide, or alkali metal cyanide such as sodium cyanide or potassium cyanide, etc. The cyanide may be used in stoichiometric amounts, although slight molar excesses may be used, preferably 0.5%-2.0%.

Step III in the reaction sequence is the hydrolysis of compound (II) to the monoamide-diacid compound (III) (partially hydrolyzed mononitrile diacid) and its spontaneous cyclization to 3KP. Compound (IV) forms readily in the presence of a base such as alkali metal or alkaline earth metal hydroxides. Preferably the base is NaOH. Mole ratios of <3.0M base:1M ED2AH$_2$ but preferably <2.0M base:1M ED2AH$_2$ are employed. Higher concentrations of base (i.e. >3.0M base:M ED-2AH$_2$) cause some disproportionation of the diacid mononitrile and some ED4A (ethylenediaminetetraacetic acid) is formed, especially at temperatures >65° C. In particular, the concentration of ED4A is found to be in direct proportion to the amount of excess caustic employed, when high temperature reactions are conducted and high molar ratios of base are employed (>2.0M base:1M ED2AH$_2$), which may be attributed to the simultaneous hydrolysis of 3KP and disproportionation of the mononitrile-diacid. When the mole ratio of base to ED2A is <2.0, higher temperatures may be used. Also, in Step III ammonia is eliminated between an amide group and an imino group on the same molecule. However, at lower temperatures (<65° C.) higher amounts of base may be employed (>2.0M) and hydrolysis of compound (II) can proceed directly to ED3A without cyclization.

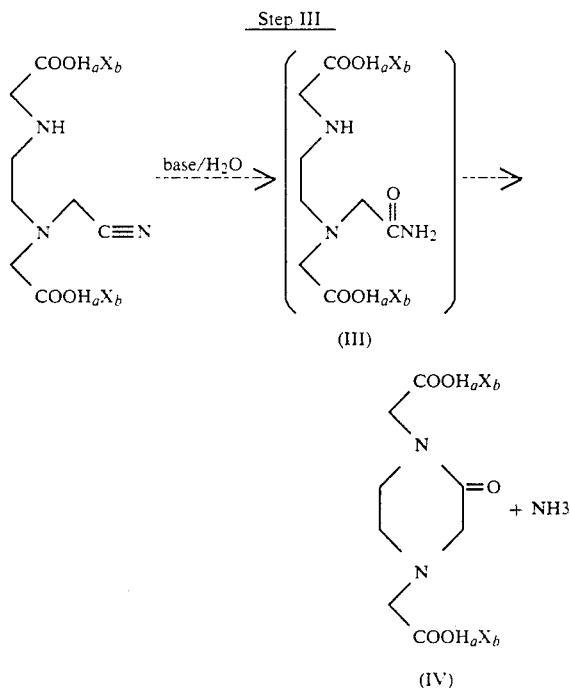

Step IV is the hydrolysis of 3KPNa$_2$ by at least the addition of 1 equivalent of caustic, preferably a 1 molar excess of caustic. This amounts to approximately 5% weight excess (free) caustic in solution on a 40% ED-3ANa$_3$ solution. The solution is boiled under atmospheric pressure to the desired concentration. Preferably the reaction is carried out by raising the temperature from the temperature in Step III to the boil over a period from about 30 minutes to about 6 hours.

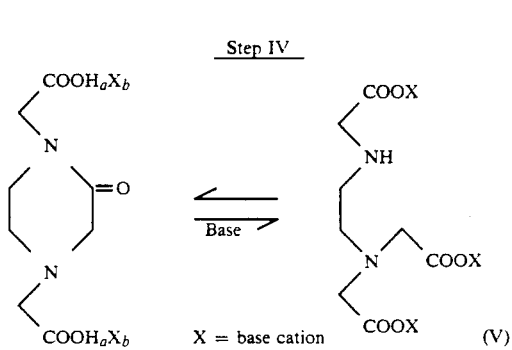

The resulting solutions typically give approximately 35-40% ED3ANa$_3$, with approximately 2% 3KPNa$_2$ remaining as an unopened ringed structure. This corresponds to about a 94% conversion to ED3ANa$_3$, with the remaining 6% of mass existing as 3KPNa$_2$. Acidification of this mass to pH's <6.0 to produce ED3AH$_3$ is not possible, as cyclization to 3KPH$_2$ will eventually occur.

The foregoing synthetic scheme results in conversions to ED3ANa$_3$ in excess of 90%, with the residual proportion being 3KPNa$_2$ to give a total mass balance of virtually 100%. The reactions are tolerant to a wide pH range.

In an alternative embodiment, the starting material is ED2AH$_a$X$_b$, where x is a base, e.g., an alkali or alkaline earth metal, a is 1 to 2, and b is 0 to 1 in aqueous solutions. The reaction mixture also can be acidified with acids having pK$_a$'s less than or equal to 3, prior to during or after the addition of a cyanide source, to ensure complete formation of carboxymethyl-2-oxopiperazine (the lactam). Formaldehyde is added, essentially resulting in the hydroxymethyl derivative. Upon the addition of a cyanide source, 1-cyanomethyl-4-carboxymethyl-2-ketopiperazine or a salt thereof is formed, and can be isolated in good yield in crystalline form by conventional means after cooling the reaction mixture. Conversions are quantitative. Furthermore, in place of CH$_2$O and a cyanide source, HOCH$_2$CN, which is the reaction product of formaldehyde and cyanide, may also be employed in this method. Upon the addition of any suitable base or acid, this material may be hydrolyzed to 3KP. The addition of a base (>2.0 equivalents but preferably greater than or equal to 3.0 equivalents will open this ring structure to form the salt of ED3A. Heating the reaction mixture will enhance the rate of reaction.

The overall reaction scheme is shown below:

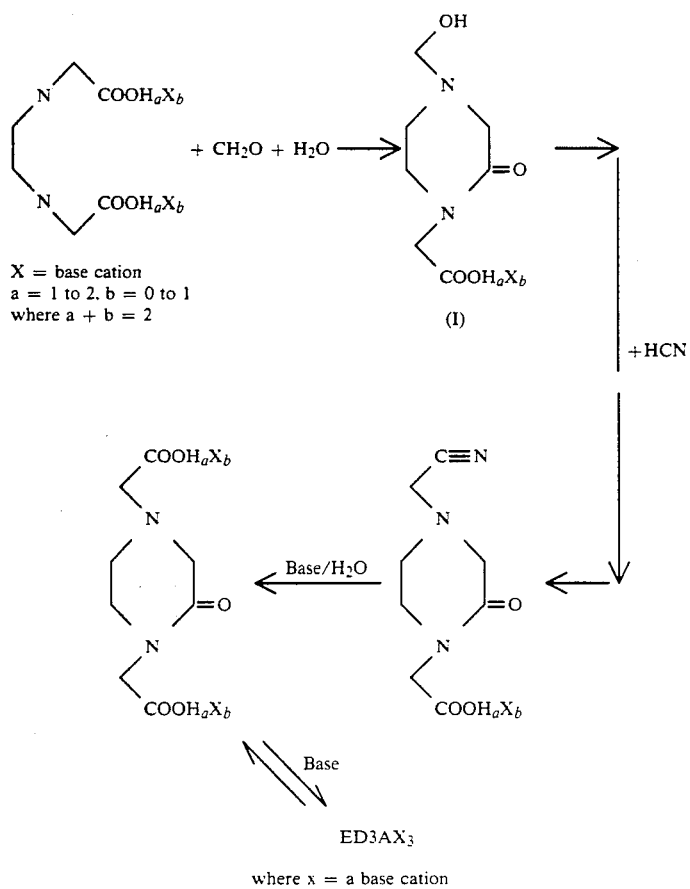

where x = a base cation

In a further embodiment, EDDA is allowed to form the lactam (carboxymethyl-2-oxo-piperazine) by acidification, and the lactam is reacted with chloro or bromo acetic acid to form ED3A or 3KP.

The following procedure to obtain $ED2AH_2$ was for experimental purposes only. Far less elaborate schemes for the production of $ED2AH_2$ are possible. Any schemes known in the art can be employed for the production of $ED2AH_2$ and its salts, and the instant invention is not to be limited by any particular scheme.

In the following examples, all batches were synthesized from $EDDAH_2$ (98.20%) obtained by acidification of $EDDANa_2$ to a pH of 5.50 with nitric acid, while maintaining the temperature of the solution $<10°$ C. The resultant slurry was filtered by means of a Buchner funnel with the vacuum provided by a water aspirator. The filter cake was washed with approximately 7 liters of iced $H_2O$. To enhance drying, the cake was then washed with approximately 1 liter of MeOH. The crystals were then placed on 1 inch deep stainless steel trays, dried in a Stokes vacuum dryer, model 338F at 40° C. under a vacuum of 4 mm Hg, for 12 hours. Approximately 2 Kg of a white crystalline powder was recovered. Analysis of this powder showed it to be 98.2% $ED2AH_2$.

All batches were synthesized on a 0.5 liter scale. 88 g of $ED2AH_2$ were charged to a 500 ml conical flask and diluted with 180 mls of $H_2O$. 50% caustic was used to obtain the sodium salt in the ratio required. This solution was stirred for 30 minutes, and then charged to a 1 liter 5-necked round bottom flask. The conical flask was then washed with 20 mls. of $H_2O$, and the washings transferred to the round bottom flask. The round bottom flask was equipped with a magnetic stirring bar, a condenser (ethylene glycol/$H_2O$ @ 0° C.), A 0°-250° C. mercury thermometer, and a J-type thermocouple that provided a signal to a Love proportional controller, which maintained the temperature at the desired level were employed. A Glass-Col heating mantle controlled by the Love controller via a Powerstat variable autotransformer was used to heat the contents of the flask. 37% $CH_2O$ and 100% HCN were pumped at approximately 1 g/minute and 0.50 g/minute, respectively, by an FMI micro metering pump at a setting of 0.5, via $\frac{1}{8}''$ Teflon tubing to the flask. A 125 ml addition funnel equipped with a Teflon metering valve, and a condenser with the same coolant as described above, was used as the reservoir for the reactants to be pumped. Table 1 shows the results for the experiments conducted up to stage 3 of the reaction. Table 2 shows results for ED3A produced for 9 conditions.

TABLE 1

| Exp | Tot wt | Comments | temp | t (mins) | Moles EDDA | % EDDANa2 Ic 220.00 | % EDDANa3 Ic 300.00 | % 3KPNa2 Ic 260.00 | % EDDA to Produc | % Unrxt EDDA | Mass balance |
|---|---|---|---|---|---|---|---|---|---|---|---|
| 1-0 | 240.75 | 2NaOH/1EDDA | 50 | 0.0 | 0.247 | 22.57% | 0.00% | 0.00% | 0.00% | 100.00% | 100.00% |
| 1-1 | 238.98 | 50° C. | 50 | 55.0 | 0.245 | 4.36% | 0.30% | 11.68% | 44.76% | 19.32% | 64.08% |
| 1-2 | 234.04 | | 50 | 102.0 | 0.240 | 3.03% | 0.50% | 15.15% | 58.42% | 13.42% | 71.84% |
| 1-3 | 228.13 | | 50 | 144.0 | 0.234 | 2.13% | 0.60% | 17.50% | 67.55% | 9.44% | 76.99% |
| 1-4 | 221.69 | | 50 | 199.0 | 0.227 | 1.51% | | 19.21% | 72.02% | 6.69% | 78.71% |
| 1-5 | 214.52 | | 50 | 250.0 | 0.220 | 1.14% | | 20.54% | 77.00% | 5.05% | 82.05% |
| 1-6 | 208.17 | | 50 | 300.0 | 0.214 | 0.89% | 1.20% | 20.90% | 82.25% | 3.94% | 86.19% |
| final so | 202.88 | | | | | | | | | | |
| 2-0 | 240.75 | 2NaOH/1EDDA | 65 | 0.0 | 0.247 | 22.57% | | 0.00% | 0.00% | 100.00% | 100.00% |
| 2-1 | 240.75 | 65° C. | 65 | 15.0 | 0.247 | 3.84% | | 13.94% | 52.26% | 17.01% | 69.27% |
| 2-2 | 236.21 | | 65 | 45.0 | 0.242 | 2.58% | | 17.68% | 66.28% | 11.43% | 77.71% |
| 2-3 | 231.19 | | 65 | 90.0 | 0.237 | 1.49% | | 20.89% | 78.31% | 6.60% | 84.91% |
| 2-4 | 226.19 | | 65 | 135.0 | 0.232 | 1.45% | | 21.64% | 81.12% | 6.42% | 87.55% |
| 2-5 | 220.81 | | 65 | 186.0 | 0.227 | 1.41% | | 21.81% | 81.76% | 6.25% | 88.01% |
| 2-6 | 214.61 | | 65 | 230.0 | 0.220 | 1.36% | | 21.73% | 81.46% | 6.03% | 87.49% |
| 2-7 | 210.35 | | 65 | 262.0 | 0.216 | 1.28% | | 21.74% | 81.50% | 5.67% | 87.17% |
| 2-8 | 205.34 | | 65 | 990.0 | 0.211 | 1.23% | | 21.60% | 80.97% | 5.45% | 86.42% |
| final so | 197.00 | | | | | | | | | | |
| 3-0 | 240.75 | 2NaOH/1EDDA | 80 | 0.0 | 0.247 | 22.57% | | 0.00% | 0.00% | 100.00% | 100.00% |
| 3-1 | 239.86 | 80° C. | 80 | 10.0 | 0.246 | 4.16% | | 15.92% | 59.68% | 18.43% | 78.11% |
| 3-2 | 235.19 | | 80 | 35.0 | 0.241 | 3.66% | | 18.86% | 69.95% | 16.22% | 86.17% |
| 3-3 | 229.91 | | 80 | 75.0 | 0.236 | 3.33% | | 19.61% | 73.51% | 14.75% | 88.27% |
| 3-4 | 223.28 | | 80 | 136.0 | 0.229 | 3.04% | | 19.50% | 73.10% | 13.47% | 86.57% |
| 3-5 | 217.66 | | 80 | 210.0 | 0.223 | 2.89% | | 19.77% | 74.11% | 12.80% | 86.92% |
| 3-6 | 211.34 | | 80 | 280.0 | 0.217 | 2.69% | | 19.99% | 74.94% | 11.92% | 86.86% |
| final so | 105.07 | | | | | | | | | | |
| 4-0 | 239.10 | 1.9NaOH/1EDDA | 50 | 0.0 | 0.247 | 22.73% | | 0.00% | 0.00% | 100.00% | 100.00% |
| 4-1 | 239.10 | 50° C. | 50 | 30.0 | 0.246 | 6.73% | | 6.34% | 23.60% | 29.61% | 53.22% |
| 4-2 | 234.00 | 1.0 CH2O | 50 | 70.0 | 0.242 | 5.00% | | 10.24% | 38.12% | 22.00% | 60.13% |
| 4-3 | 228.81 | | 50 | 115.0 | 0.236 | 4.18% | | 13.58% | 50.56% | 18.39% | 68.95% |
| 4-4 | 223.25 | | 50 | 165.0 | 0.231 | 2.68% | | 16.40% | 61.06% | 11.79% | 72.85% |
| 4-5 | 217.35 | | 50 | 200.0 | 0.225 | 2.16% | | 17.99% | 66.98% | 9.50% | 76.48% |
| 4-6 | 212.72 | | 50 | 250.0 | 0.220 | 1.52% | | 19.66% | 73.20% | 6.69% | 79.89% |
| 4-7 | 208.46 | | 50 | 285.0 | 0.215 | 1.14% | 1.10% | 20.75% | 77.26% | 5.02% | 82.27% |
| 4-8 | 192.50 | | 50 | 1280.0 | 0.199 | 0.13% | | 23.50% | 91.04% | 0.57% | 91.62% |
| final so | 138.00 | | boiled | | 0.201 | 0.13% | | 32.75% | 86.36% | 0.41% | 86.77% |
| 5-0 | 241.10 | 2.1NaOH/1EDDA | 50 | 0 | 0.247 | 22.54% | 0.00% | 0.00% | 0.00% | 100.00% | 100.00% |
| 5-1 | 241.10 | 50° C. | 50 | 40.0 | 0.247 | 5.58% | 0.10% | 9.35% | 35.43% | 24.76% | 60.19% |
| 5-2 | 236.01 | 1.05 CH2O | 50 | 90.0 | 0.242 | 3.85% | 0.20% | 14.31% | 54.37% | 17.08% | 71.46% |
| 5-3 | 231.32 | | 50 | 138.0 | 0.237 | 2.75% | 0.50% | 17.20% | 66.20% | 12.20% | 78.40% |
| 5-4 | 225.41 | | 50 | 186.0 | 0.231 | 2.15% | 0.80% | 18.60% | 72.43% | 9.54% | 81.97% |
| 5-5 | 220.92 | | 50 | 228.0 | 0.226 | 1.71% | 1.00% | 19.41% | 76.12% | 7.59% | 83.71% |
| 5-6 | 216.39 | | 50 | 260.0 | 0.222 | 1.49% | 1.30% | 19.85% | 78.75% | 6.61% | 85.36% |
| 5-7 | 211.83 | | 50 | 1350.0 | 0.217 | 0.66% | 3.40% | 16.01% | 71.17% | 2.93% | 74.10% |
| final so | 170.21 | | boiled | | 0.220 | 0.92% | 5.10% | 23.10% | 82.02% | 3.24% | 85.26% |
| 5-0 | 239.10 | 1.9NaOH/1EDDA | 80 | 0.0 | 0.247 | 22.73% | 0.00% | 0.00% | 0.00% | 100.00% | 100.00% |
| 5-1 | 239.10 | 80° C. | 80 | 15.0 | 0.247 | 3.61% | | 17.05% | 63.48% | 15.88% | 79.36% |
| 5-2 | 233.80 | 1.05 CH2O | 80 | 45.0 | 0.242 | 3.01% | | 18.70% | 69.62% | 13.24% | 82.87% |
| 5-3 | 229.09 | | 80 | 90.0 | 0.237 | 2.61% | | 19.78% | 73.64% | 11.48% | 85.13% |
| 5-4 | 222.74 | | 80 | 145.0 | 0.230 | 2.26% | | 20.36% | 75.80% | 9.94% | 85.75% |

TABLE 1-continued

| Exp | Tot wt | Comments | temp | t (mins) | Moles EDDA | % EDDANa2 | % EDDANa3 | % 3KPNa2 | % EDDA to Produc | % Unrxt EDDA | Mass balance |
|---|---|---|---|---|---|---|---|---|---|---|---|
| 5-5 | 217.86 | | 80 | 189.0 | 0.225 | 1.32% | | 20.11% | 74.87% | 5.81% | 80.68% |
| 5-6 | 213.47 | | 80 | 240.0 | 0.221 | 1.60% | | 18.25% | 67.98% | 7.04% | 75.02% |
| 5-7 | 208.33 | | 80 | 285.0 | 0.215 | 1.66% | | 21.35% | 79.49% | 7.30% | 86.79% |
| 5-8 | 203.47 | | 80 | 1282.0 | 0.210 | 0.40% | 0.10% | 20.90% | 78.14% | 1.76% | 79.90% |
| 5-9 | 157.60 | | boiled | | 0.213 | 0.60% | 0.50% | 27.75% | 80.30% | 2.02% | 82.32% |
| 6-0 | 241.10 | 2.1NaOH/1EDDA | 80 | 0.0 | 0.247 | 22.54% | 0.00% | 0.00% | 0.00% | 100.00% | 100.00% |
| 6-1 | 241.10 | 80° C. | 80 | 20.0 | 0.247 | 3.72% | 1.00% | 18.17% | 71.47% | 16.51% | 87.97% |
| 6-2 | 235.20 | 1.00 CH2O | 80 | 74.0 | 0.241 | 3.44% | 1.00% | 19.09% | 74.92% | 15.26% | 90.19% |
| 6-3 | 229.95 | | 80 | 110.0 | 0.236 | 3.47% | 1.00% | 19.15% | 75.15% | 15.40% | 90.54% |
| 6-4 | 225.49 | | 80 | 155.0 | 0.231 | 3.37% | 1.00% | 19.44% | 76.24% | 14.95% | 91.19% |
| 6-5 | 220.51 | | 80 | 200.0 | 0.226 | 3.14% | 1.00% | 19.06% | 74.81% | 13.93% | 88.74% |
| 6-6 | 215.06 | | 80 | 238.0 | 0.220 | 3.15% | 1.00% | 19.20% | 75.34% | 13.98% | 89.31% |
| 6-7 | 210.36 | | 80 | 286.0 | 0.216 | 3.06% | 1.00% | 18.81% | 73.87% | 13.58% | 87.45% |
| 6-8 | 204.01 | | 80 | 320.0 | 0.209 | 3.08% | 1.00% | 19.19% | 75.30% | 13.67% | 88.96% |
| 6-9 | 198.58 | | 80 | 1286.0 | 0.203 | 2.30% | 1.70% | 19.39% | 78.33% | 10.20% | 88.53% |
| 6-10 | 145.33 | | boiled | | 0.206 | 2.49% | 1.80% | 21.94% | 63.79% | 7.99% | 71.78% |
| 7-0 | 239.10 | 1.9NaOH/1EDDA | 80 | 0.0 | 0.247 | 22.73% | | 0.00% | 0.00% | 100.00% | 100.00% |
| 7-1 | 239.10 | 80° C. | 80 | 26.0 | 0.247 | 3.32% | | 16.83% | 62.66% | 14.61% | 77.27% |
| 7-2 | 233.84 | 1.00 CH2O | 80 | 71.0 | 0.242 | 2.87% | | 19.69% | 73.31% | 12.63% | 85.94% |
| 7-3 | 228.66 | | 80 | 119.0 | 0.236 | 2.42% | | 19.79% | 73.68% | 10.65% | 84.33% |
| 7-4 | 223.62 | | 80 | 160.0 | 0.231 | 2.31% | | 20.21% | 75.24% | 10.16% | 85.41% |
| 7-5 | 218.59 | | 80 | 208.0 | 0.226 | 1.99% | | 20.36% | 75.80% | 8.76% | 84.56% |
| 7-6 | 213.40 | | 80 | 260.0 | 0.220 | 1.88% | | 20.24% | 75.36% | 8.27% | 83.63% |
| 7-7 | 207.57 | | 80 | 1291.0 | 0.214 | 0.51% | | 19.85% | 73.90% | 2.24% | 76.15% |
| 7-8 | 124.44 | | boiled | | 0.217 | 0.94% | 1.80% | 30.58% | 72.60% | 2.51% | 75.11% |
| 8-0 | 239.10 | 1.9NaOH/1EDDA | 50 | 0.0 | 0.247 | 22.73% | | 0.00% | 0.00% | 100.00% | 100.00% |
| 8-1 | 239.10 | 50° C. | 50 | 35.0 | 0.247 | 1.89% | | 20.44% | 76.10% | 8.32% | 84.42% |
| 8-2 | 233.30 | 1.05 CH2O | 50 | 117.0 | 0.241 | 1.29% | | 22.46% | 83.62% | 5.68% | 89.30% |
| 8-3 | 228.81 | | 50 | 160.0 | 0.236 | 1.07% | | 23.18% | 86.30% | 4.71% | 91.01% |
| 8-4 | 223.96 | | 50 | 210.0 | 0.231 | 0.82% | | 23.29% | 86.71% | 3.61% | 90.32% |
| 8-5 | 218.87 | | 50 | 297.0 | 0.226 | 0.56% | | 24.16% | 89.95% | 2.46% | 92.42% |
| 8-6 | 199.40 | | 50 | 1261.0 | 0.206 | 0.24% | | 24.96% | 92.93% | 1.06% | 93.99% |
| 8-7 | 141.00 | | boiled | | 0.206 | 0.27% | 1.10% | 35.02% | 94.71% | 0.84% | 95.55% |
| 9-0 | 241.10 | 2.1NaOH/1EDDA | 50 | 0.0 | 0.247 | 22.54% | | 0.00% | 0.00% | 100.00% | 100.00% |
| 9-1 | 241.10 | 50° C. | 50 | 30.0 | 0.247 | | 0 | 9.07% | 34.05% | 0.00% | 34.05% |
| 9-2 | 235.44 | 1.00 CH2O | 50 | 112.0 | 0.241 | 2.71% | 0.60% | 16.04% | 62.17% | 12.02% | 74.19% |
| 9-3 | 230.22 | | 50 | 168.0 | 0.236 | 2.10% | 0.70% | 18.36% | 71.21% | 9.32% | 80.52% |
| 9-4 | 225.60 | | 50 | 211.0 | 0.231 | 1.55% | 1.10% | 19.28% | 75.96% | 6.88% | 82.84% |
| 9-5 | 220.60 | | 50 | 250.0 | 0.226 | 1.02% | 1.20% | 20.77% | 81.88% | 4.53% | 86.41% |
| 9-6 | 214.87 | | 50 | 240.0 | 0.220 | 0.89% | 3.30% | 20.16% | 86.42% | 3.95% | 90.37% |
| 9-7 | 112.00 | | boiled | | 0.223 | 1.51% | 0.60% | 34.28% | 82.36% | 3.45% | 85.81% |
| 10-0 | 241.10 | 2.1NaOH/1EDDA | 80 | 0.0 | 0.247 | 22.54% | 0 | 0.00% | 0.00% | 100.00% | 100.00% |
| 10-1 | 241.10 | 80° C. | 80 | 30.0 | 0.247 | 3.82% | 0.70% | 19.28% | 74.66% | 16.95% | 91.61% |
| 10-2 | 236.36 | 1.05 CH2O | 80 | 88.0 | 0.242 | 3.42% | 0.60% | 19.50% | 75.16% | 15.17% | 90.33% |
| 10-3 | 231.84 | | 80 | 133.0 | 0.238 | 3.32% | 0.80% | 20.04% | 77.84% | 14.73% | 92.57% |
| 10-4 | 226.84 | | 80 | 196.0 | 0.232 | 2.99% | 0.50% | 17.77% | 68.34% | 13.27% | 81.61% |
| 10-5 | 221.45 | | 80 | 240.0 | 0.227 | 3.21% | 0.70% | 20.42% | 78.94% | 14.24% | 93.18% |
| 10-6 | 216.41 | | 80 | 293.0 | 0.222 | 3.09% | 0.01% | 19.99% | 75.07% | 13.71% | 88.78% |
| 10-7 | 210.56 | | 80 | 1290.0 | 0.216 | 2.16% | 1.00% | 19.30% | 75.71% | 9.58% | 85.30% |
| 10-8 | 138.64 | | boiled | | 0.218 | 3.22% | 2.50% | 28.68% | 75.34% | 9.29% | 84.63% |
| 11-0 | 263.10 | 3.1NaOH/1EDDA | 35 | 0.0 | 0.247 | 20.65% | 0.00% | 0 | 0.00% | 100.00% | 100.00% |

TABLE 1-continued

| Exp | Tot wt | Comments | temp | t (mins) | Moles EDDA | % EDDANa2 | % EDDANa3 | % 3KPNa2 | % EDDA to Produc | % Unrxt EDDA | Mass balance |
|---|---|---|---|---|---|---|---|---|---|---|---|
| 11-1 | 263.10 | 35° C. | 35 | 35.0 | 0.247 | 8.47% | | 2.37% | 9.71% | 41.01% | 50.72% |
| 11-2 | 258.10 | 1.00 CH2O | 35 | 72.0 | 0.242 | | | 4.89% | 20.03% | 0.00% | 20.03% |
| 11-3 | 252.90 | | 35 | 143.0 | 0.237 | | | 6.40% | 26.22% | 34.91% | 61.13% |
| 11-4 | 247.40 | | 35 | 182.0 | 0.232 | 7.21% | 0.60% | 6.81% | 30.03% | 34.86% | 64.89% |
| 11-5 | 242.74 | | 35 | 221.0 | 0.228 | 7.20% | 0.70% | 8.25% | 36.28% | 33.36% | 69.64% |
| 11-6 | 238.43 | | 35 | 257.0 | 0.224 | 6.89% | 1.10% | 9.49% | 42.78% | 31.96% | 74.74% |
| 11-7 | 233.63 | | 35 | 1360.0 | 0.219 | 6.60% | 12.00% | 9.08% | 79.81% | 13.94% | 93.75% |
| 11-8 | 140.00 | | boiled | | 0.222 | 2.88% | 34.30% | 5.27% | 84.89% | 12.10% | 96.98% |
| 12-0 | 263.10 | 3.1NaOH/1EDDA | 50 | 0.0 | 0.247 | 4.22% | 0.00% | 0.00% | 0.00% | 100.00% | 100.00% |
| 12-1 | 236.10 | 50° C. | 50 | 13.0 | 0.247 | 20.65% | 0.40% | 12.39% | 52.18% | 30.02% | 82.20% |
| 12-2 | 257.27 | 1.00 CH2O | 50 | 54.0 | 0.242 | 6.20% | 1.80% | 11.35% | 52.89% | 29.24% | 82.13% |
| 12-3 | 251.81 | | 50 | 98.0 | 0.236 | 6.04% | 3.50% | 12.49% | 63.60% | 23.43% | 87.03% |
| 12-4 | 247.54 | | 50 | 147.0 | 0.232 | 4.84% | 4.90% | 12.90% | 70.25% | 20.43% | 90.68% |
| 12-5 | 243.10 | | 50 | 1237.0 | 0.228 | 3.47% | 15.90% | 8.07% | 89.52% | 16.80% | 106.32% |
| 12-6 | 138.80 | | boiled | | 0.231 | 5.50% | 40.00% | 5.45% | 92.71% | 15.02% | 107.73% |
| 13-0 | 271.10 | 3.5NaOH/1EDDA | 35 | 0.0 | 0.247 | 20.04% | 0.00% | 0 | 0.00% | 100.00% | 100.00% |
| 13-1 | 265.99 | 35° C. | 35 | 10.0 | 0.247 | 9.60% | | 4.02% | 16.97% | 47.89% | 64.86% |
| 13-2 | 261.37 | 1.00 CH2O | 35 | 47.0 | 0.242 | 7.82% | | 8.07% | 34.07% | 39.01% | 73.08% |
| 13-3 | 261.37 | | 35 | 90.0 | 0.238 | 7.31% | | 9.19% | 38.79% | 36.47% | 75.26% |
| 13-4 | 256.60 | | 35 | 130.0 | 0.234 | 6.70% | 0.80% | 9.46% | 42.86% | 33.43% | 76.29% |
| 13-5 | 252.16 | | 35 | 186.0 | 0.230 | 6.35% | 0.80% | 10.36% | 46.66% | 31.68% | 78.34% |
| 13-6 | 246.06 | | 35 | 230.0 | 0.224 | 6.12% | 1.40% | 10.54% | 49.62% | 30.53% | 80.15% |
| 13-7 | 241.06 | | 35 | 308.0 | 0.220 | 6.16% | 2.30% | 10.43% | 52.44% | 30.73% | 83.18% |
| 13-8 | 235.25 | | 35 | 1320.0 | 0.214 | 2.52% | 13.90% | 6.98% | 80.32% | 12.57% | 92.89% |
| 14-0 burned | 443.96 | 1.8NaOH/1EDDA | 65 | 13.0 | 0.491 | | | 5.38% | 18.71% | 0.00% | 18.71% |
| 14-1 | 442.63 | 65° C. | 65 | 49.0 | 0.490 | | | 10.48% | 36.45% | 0.00% | 36.45% |
| 14-2 | 440.98 | 1.00 CH2O | 65 | 107.0 | 0.488 | | | 16.17% | 56.23% | 0.00% | 56.23% |
| 14-3 | 439.19 | | 65 | 1063.0 | 0.486 | | | 21.12% | 73.45% | 0.00% | 73.45% |
| 15-0 | 448.82 | 1.9NaOH/1EDDA | 50 | 25.0 | 0.491 | | | 2.05% | 7.21% | 0.00% | 7.21% |
| 15-1 | 447.52 | 50° C. | 50 | 85.0 | 0.490 | | | 7.06% | 24.82% | 0.00% | 24.82% |
| 15-2 | 446.05 | 1.05 CH2O | 50 | 122.0 | 0.488 | | | 9.97% | 35.05% | 0.00% | 35.05% |
| 15-3 | 444.25 | | 50 | 173.0 | 0.486 | | | 13.01% | 45.74% | 0.00% | 45.74% |
| 15-4 | 443.14 | | 50 | 1238.0 | 0.485 | | | 25.10% | 88.25% | 0.00% | 88.25% |
| 15-5 | 441.95 | | 50 | | 0.485 | | | 25.52% | 89.48% | 0.00% | 89.48% |
| 16-0 | 450.68 | 1.9NaOH/1EDDA | 65 | 10.0 | 0.491 | | | 6.67% | 23.55% | 0.00% | 23.55% |
| 16-1 | 449.03 | 65° C. | 65 | 41.0 | 0.489 | | | 12.47% | 44.02% | 0.00% | 44.02% |
| 16-2 | 447.46 | 1.00 CH2O | 65 | 82.0 | 0.487 | | | 17.76% | 62.70% | 0.00% | 62.70% |
| 16-3 | 446.18 | | 65 | 125.0 | 0.486 | | | 20.24% | 71.45% | 0.00% | 71.45% |
| 16-4 | 444.85 | | 65 | 1080.0 | 0.486 | | | 24.22% | 85.25% | 0.00% | 85.25% |
| 17-0 | 450.70 | 1.9NaOH/1EDDA | 75 | 17.0 | 0.491 | | | 14.87% | 52.50% | 0.00% | 52.50% |
| 17-1 | 449.45 | 75° C. | 75 | 46.0 | 0.490 | | | 20.66% | 72.94% | 0.00% | 72.94% |
| 17-2 | 448.35 | 1.05 CH2O | 75 | 98.0 | 0.486 | | | 24.26% | 85.65% | 0.00% | 85.65% |
| 17-3 | 447.08 | | 75 | 239.0 | 0.487 | | | 24.97% | 88.16% | 0.00% | 88.16% |
| 17-4 | 445.66 | | 75 | 1233.0 | 0.486 | | | 26.24% | 92.64% | 0.00% | 92.64% |
| 17-5 | 407.20 | | boil | boil | 0.486 | | | 26.41% | 85.19% | 0.00% | 85.19% |
| 18-0 | 450.70 | 1.9NaOH/1EDDA | 50° C. | 10.0 | 0.491 | | | 1.36% | 4.80% | 0.00% | 4.80% |
| 18-1 | 449.36 | 50° C. | 50° C. | 88.0 | 0.490 | | | 7.60% | 26.83% | 0.00% | 26.83% |
| 18-2 | 447.82 | 1.00 CH2O | 50° C. | 1365.0 | 0.488 | | | 24.34% | 85.93% | 0.00% | 85.93% |
| 18-3 | 392.30 | | boil | boil | 0.488 | | | 27.84% | 86.10% | 0.00% | 86.10% |
| 19-0 | 446.70 | 1.8NaOH/1EDDA | 50° C. | 41.0 | 0.491 | | | 2.59% | 9.06% | 0.00% | 9.06% |

TABLE 1-continued

| Exp | Tot wt | Comments | temp | t (mins) | Moles EDDA | Ic % EDDANa2 | Ic % EDDANa3 | Ic % 3KPNa2 | % EDDA to Produc | % Unrxt EDDA | Mass balance |
|---|---|---|---|---|---|---|---|---|---|---|---|
| 19-1 | 445.33 | 50° C. | 50° C. | 120.0 | 0.489 | | | 8.63% | 30.20% | 0.00% | 30.20% |
| 19-2 | 443.88 | 1.00 CH2O | 50° C. | 164.0 | 0.488 | | | 11.36% | 39.75% | 0.00% | 39.75% |
| 19-3 | 442.48 | | 50° C. | 1400.0 | 0.486 | | | 24.71% | 86.46% | 0.00% | 86.46% |
| 19-4 | 343.20 | | boil | boil | 0.486 | | | 31.79% | 86.28% | 0.00% | 86.28% |
| 20-0 | 446.07 | 1.8NaOH/1EDDA | 50° C. | 60.0 | 0.491 | | | 3.35% | 11.71% | 0.00% | 11.71% |
| 20-1 | 444.76 | 50° C. | 50° C. | 210.0 | 0.490 | | | 13.30% | 46.47% | 0.00% | 46.47% |
| 20-2 | 442.90 | 1.05 CH2O | 50° C. | 300.0 | 0.488 | | | 16.72% | 58.42% | 0.00% | 58.42% |
| 20-3 | 441.42 | | 50° C. | 1250.0 | 0.486 | | | 24.46% | 85.47% | 0.00% | 85.47% |
| 20-4 | 353.40 | | boil | boil | 0.486 | | | 30.81% | 86.19% | 0.00% | 86.19% |
| 21-0 | 446.70 | 1.8NaOH/1EDDA | 65° C. | 16.0 | 0.491 | | | 7.03% | 24.60% | 0.00% | 24.60% |
| 21-1 | 444.89 | 65° C. | 65° C. | 85.0 | 0.489 | | | 17.26% | 60.40% | 0.00% | 60.40% |
| 21-2 | 443.09 | 1.05 CH2O | 65° C. | 175.0 | 0.487 | | | 22.05% | 77.16% | 0.00% | 77.16% |
| 21-3 | 441.24 | | 65° C. | 253.0 | 0.485 | | | 23.83% | 83.38% | 0.00% | 83.38% |
| 21-4 | 439.56 | | 65° C. | 1240.0 | 0.483 | | | 24.40% | 85.38% | 0.00% | 85.38% |
| 21-5 | 380.00 | | boil | boil | 0.483 | | | 24.96% | 75.50% | 0.00% | 75.50% |
| 22-0 | 446.70 | 1.8NaOH/1EDDA | 65° C. | 25.0 | 0.491 | | | 9.99% | 34.96% | 0.00% | 34.96% |
| 22-1 | 444.33 | 65° C. | 65° C. | 110.0 | 0.488 | | | 19.71% | 68.97% | 0.00% | 68.97% |
| 22-2 | 442.74 | 1.050 CH2O | 65° C. | 165.0 | 0.487 | | | 21.34% | 74.67% | 0.00% | 74.67% |
| 22-3 | 441.04 | | 65° C. | 208.0 | 0.485 | | | 21.40% | 74.88% | 0.00% | 74.88% |
| 22-4 | 439.65 | | 65° C. | 1292.0 | 0.483 | | | 23.72% | 83.00% | 0.00% | 83.00% |
| 22-5 | 394.70 | | boil | boil | 0.483 | | | 25.87% | 81.27% | 0.00% | 81.27% |
| 23-0 | 450.70 | 1.9NaOH/1EDDA | 65° C. | 33.0 | 0.491 | | | 11.14% | 39.33% | 0.00% | 39.33% |
| 23-1 | 448.95 | 65° C. | 65° C. | 92.0 | 0.489 | | | 18.65% | 65.84% | 0.00% | 65.84% |
| 23-2 | 447.21 | 1.05 CH2O | 65° C. | 148.0 | 0.487 | | | 21.69% | 76.58% | 0.00% | 76.58% |
| 23-3 | 445.41 | | 65° C. | 230.0 | 0.485 | | | 23.32% | 82.33% | 0.00% | 82.33% |
| 23-4 | 443.77 | | 65° C. | 1276.0 | 0.483 | | | 24.79% | 87.52% | 0.00% | 87.52% |
| 23-5 | 408.62 | | boil | boil | 0.483 | | | 26.43% | 85.92% | 0.00% | 85.92% |

TABLE 2

| Exp | Temp °C. | M CH2O | EDDA:NaOH | final wt | % 3KPNa2 recyclized | moles 3KP | moles after sampling | % conversion recyclized |
|---|---|---|---|---|---|---|---|---|
| 1 | 50.00 | 1.05 | 1.90 | 373.40 | 31.39% | 0.45 | 0.48 | 92.99% |
| 2 | 85.00 | 1.00 | 1.90 | 364.00 | 31.91% | 0.45 | 0.49 | 91.91% |
| 3 | 75.00 | 1.05 | 1.90 | 376.40 | 29.53% | 0.43 | 0.49 | 88.04% |
| 4 | 50.00 | 1.00 | 1.90 | 372.80 | 31.77% | 0.48 | 0.49 | 93.37% |
| 5 | 50.00 | 1.00 | 1.80 | 370.30 | 32.10% | 0.46 | 0.49 | 94.00% |
| 6 | 50.00 | 1.05 | 1.80 | 388.95 | 30.89% | 0.46 | 0.49 | 94.41% |
| 7 | 65.00 | 1.05 | 1.80 | 393.60 | 29.71% | 0.45 | 0.48 | 93.07% |
| 8 | 65.00 | 1.00 | 1.80 | 415.60 | 26.86% | 0.43 | 0.48 | 88.82% |
| 9 | 65.00 | 1.05 | 1.90 | 417.70 | 29.82% | 0.48 | 0.48 | 99.08% |

| Exp | % 3KPNA2 after stage | % difference 1st 1-recycle | % unopened 3KPNa2 | % ED3ANa3 by titr | % conversion to ED3ANa3 | % total on ED3A |
|---|---|---|---|---|---|---|
| 1 | 89.48% | −3.51% | 2.05% | 36.00% | 91.26% | 95.74% |
| 2 | 85.25% | −6.85% | 1.88% | 38.32% | 94.89% | 98.23% |
| 3 | 85.19% | −2.85% | 2.09% | 36.55% | 93.40% | 97.87% |
| 4 | 86.10% | −7.27% | 2.17% | 38.16% | 96.58% | 100.87% |
| 5 | 86.28% | −7.72% | 2.28% | 37.50% | 94.27% | 98.99% |
| 6 | 86.19% | −8.22% | 2.59% | 35.39% | 93.45% | 99.10% |
| 7 | 85.38% | −7.69% | 2.85% | 34.13% | 91.20% | 98.76% |
| 8 | 81.27% | −7.55% | 3.08% | 32.54% | 91.81% | 100.56% |
| 9 | 85.92% | −13.16% | 2.43% | 32.10% | 91.03% | 97.70% |

The data demonstrate that both mass balances and conversions to product are excellent. ED3A was measured by copper(II) salt titration, and 3KP was measured by high pressure liquid chromatography (HPLC). The final column in the Table 1 shows the mass balances for stage 3 of the reaction. The 9th column in Table 2 shows the percent conversion to product based on recyclization. Recyclization was achieved by acidifying a sample of the reaction mass with HCl to a pH of 2.0. These samples were then allowed to stand in an oven at 40° C. overnight an then on a bench at room temperature for 2 days prior to analysis. This technique was employed to verify the titration results, ensuring that all product was recyclized to 3KPH$_2$. Mass balances are not as good as those that were titrated, and this may be attributed to HPLC error and dilution error, etc.

In the second embodiment of the instant invention, ED2AH$_2$ was slurried with water. 37% CH$_2$O and HCN were added in the same manner as previous runs. No salts were present. It was found that the reaction proceeded as described in the second embodiment of the invention. The ED2AH$_2$, water and formaldehyde reacted to give the hydroxymethyl derivative of the lactam, which in turn reacted with HCN to give the cyclized mono-nitrile-monoacid. This solution was allowed to react overnight at 65° C. and one large peak was found on the chromatograms upon analysis by HPLC, which was later confirmed to be 1-cyanomethyl-4-carboxymethyl-2-ketopiperazine. The batch was then split in two. When the solution was cooled to <50° C., crystals precipitated which were subsequently isolated in approximately 70% yield. The other half of the batch was hydrolyzed with caustic (2:1 mole ratio, NaOH:EDDA), NH$_3$ was liberated, and it was found that 3KPNa$_2$ was the only product. This suggests the material was the mono-nitrile-diacid. Final confirmation of this structure was successfully conducted by C$^{13}$ NMR. No attempts were made to enhance the recovery of the crystals, which is easily performed by concentration, pH adjustment, further cooling, etc.

A further example was carried out using glycolonitrile, as follows. 17.6 grams of EDDAH$_2$ were slurried in water. The solution was heated to about 70° C. and 5.7 grams of glycolonitrile were added. Three samples were taken approximately 20 minutes apart. Analysis of these samples by HPLC showed a progressive increase in mononitrile monoacid, however it was not quantified.

What is claimed is:

1. A process for the preparation of salts of ethylenediamine triacetic acid, comprising:
   a. reacting formaldehyde with an alkali metal or alkaline earth metal salt of ethylenediaminediacetic acid;
   b. reacting the product of step a with a cyanide source;
   c. allowing for the spontaneous cyclization of the resulting monoamide-diacid; and
   d. reacting the cyclization product of step c with at least 1 equivalent of alkali metal or alkaline earth metal hydroxide.

2. The process of claim 1, wherein the reaction of formaldehyde and ethylenediamine dialkali metal acetate is conducted at a temperature from about 0° to about 65° C.

3. The process of claim 1, wherein the reaction of formaldehyde and ethylenediamine dialkali metal acetate is conducted at a temperature from about 15° to about 65° C.

4. The process of claim 1, wherein the reaction of step b is conducted at a temperature from about 0° to about 65° C.

5. The process of claim 1, wherein the reaction of step b is conducted at a temperature from about 15° to about 65° C.

6. The process of claim 1, wherein said formaldehyde is used in a slight molar excess.

7. The process of claim 1, wherein said cyanide source is used in a slight molar excess.

8. The process of claim 1, wherein the solution in step d is heated to a boil over a period of about thirty minutes to about six hours.

9. The process of claim 1, wherein said alkali metal hydroxide is added to said cyclization product in at least a 1 molar excess.

10. The process of claim 1, wherein said cyanide source is selected from the group consisting of hydrogen cyanide and alkali metal cyanide.

* * * * *